United States Patent
Scubla et al.

(10) Patent No.: US 8,236,961 B2
(45) Date of Patent: Aug. 7, 2012

(54) PROCESS FOR THE PREPARATION OF KETO COMPOUNDS

(75) Inventors: Tiziano Scubla, Pasian Di Prato (IT); Pietro Allegrini, San Donato Milanese (IT); Eliana Rocchini, Colloredo Di Prato (IT); Caterina Napoletano, Via Repubblica (IT)

(73) Assignee: Dipharma Francis s.r.l., Baranzate (IT)

( * ) Notice: Subject to any disclaimer, the term of this patent is extended or adjusted under 35 U.S.C. 154(b) by 1119 days.

(21) Appl. No.: 12/121,294

(22) Filed: May 15, 2008

(65) Prior Publication Data

US 2008/0293948 A1 Nov. 27, 2008

(30) Foreign Application Priority Data

May 16, 2007 (IT) .............................. MI2007A0987

(51) Int. Cl.
 C07D 211/22 (2006.01)

(52) U.S. Cl. ........................................ 546/239; 546/240

(58) Field of Classification Search .................. 546/239, 546/240
 See application file for complete search history.

(56) References Cited

U.S. PATENT DOCUMENTS

| 4,254,129 A * | 3/1981 | Carr et al. ..................... 514/317 |
| 4,254,130 A * | 3/1981 | Carr et al. ..................... 514/317 |

FOREIGN PATENT DOCUMENTS

| EP | 1 260 505 A1 | 11/2002 |
| EP | 1260505 A1 | 11/2002 |
| EP | 1 616 861 A2 | 1/2006 |
| EP | 1616861 A2 | 1/2006 |
| WO | 93/21156 A1 | 10/1993 |
| WO | 9321156 A1 | 10/1993 |
| WO | 97/22344 A1 | 6/1997 |
| WO | 9722344 A1 | 6/1997 |
| WO | 97/23213 A1 | 7/1997 |
| WO | 9723213 A1 | 7/1997 |

OTHER PUBLICATIONS

Dean "Analytical chemistry Handbook" pp. 10.24-10.26 (1995).*
Solvent, Wikipedia free encyclopedia, pp. 1-10, (2011).*
Kawai, S.H. et al., "A Facile Synthesis of an Oxidation Product of Terfenadine", J. Org. Chem. 1994, 59, 2620-2622.

* cited by examiner

*Primary Examiner* — Celia Chang
(74) *Attorney, Agent, or Firm* — Griffin & Szipl, P.C.

(57) ABSTRACT

A process for the preparation of 4-[1-oxo-4-[4-(hydroxy-diphenylmethyl)-1-piperidinyl]butyl]-α,α-dimethylbenzeneacetic acid, useful as an intermediate for the preparation of fexofenadine, is provided.

4 Claims, 1 Drawing Sheet

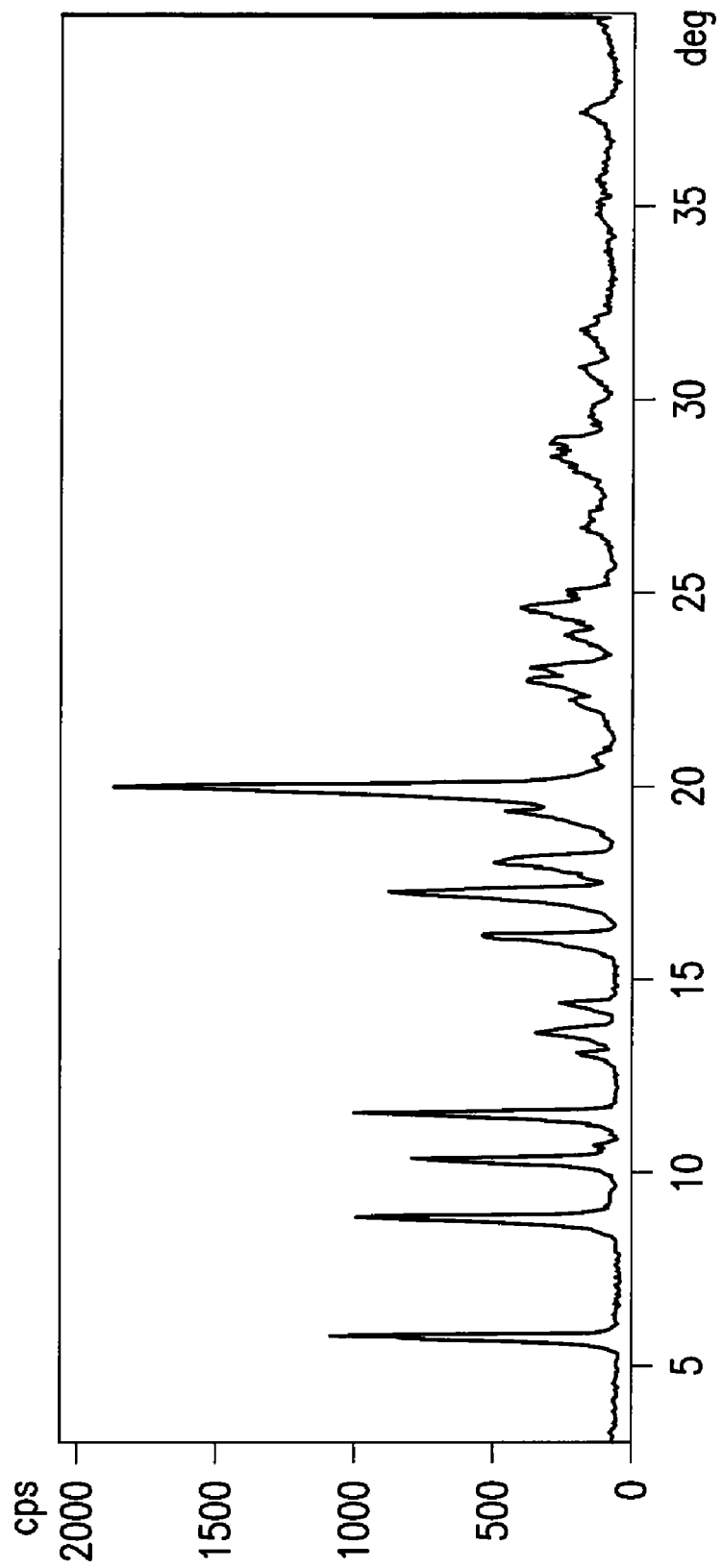

PROCESS FOR THE PREPARATION OF KETO COMPOUNDS

This application claims priority from Italian Patent Application No. MI2007A987, filed May 16, 2007, the entire disclosure of which is incorporated herein by reference.

FIELD OF THE INVENTION

The present invention relates to a novel process for the preparation of 4-[1-oxo-4-[4-(hydroxydiphenylmethyl)-1-piperidinyl]butyl]-α,α-dimethyl-benzeneacetic acid and its use in the preparation of fexofenadine.

TECHNOLOGICAL BACKGROUND OF THE INVENTION

Numerous processes for the preparation of fexofenadine are known, inter alia those disclosed in WO 93/21156, WO 97/22344 and WO 97/23213, characterized by a high number of steps. None of the known processes is based on a convergent approach, but on the construction of the molecule introducing the various functional groups step-by-step, starting from α,α-dimethylbenzeneacetic acid. An alternative route is described by Kawai S. et al. in J. Org. Chem. 1994, 59, 2620-2622, but it involves various problems which prevent its industrial application. A key step of the synthetic route is the hydration of the alkyne bond in the carboxymethyl ester of formula (A) to give the respective keto derivative of formula (B).

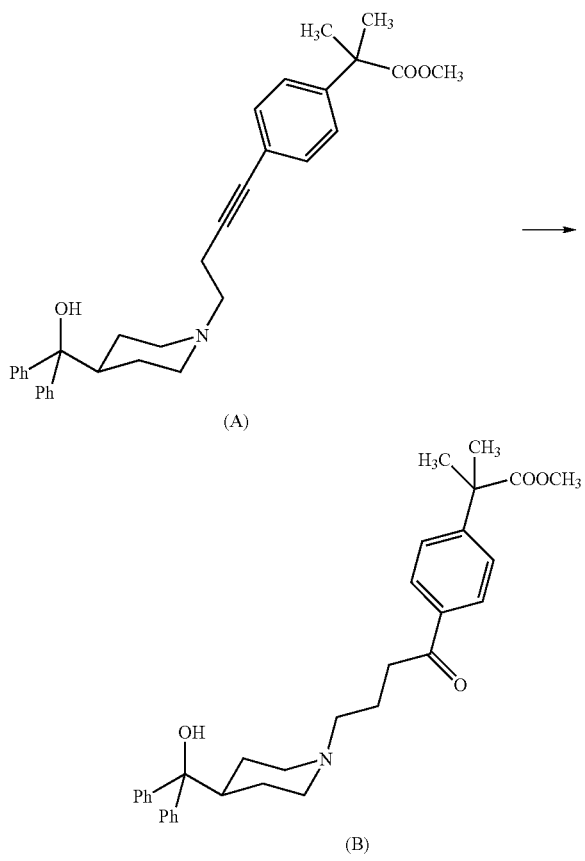

wherein Ph is a phenyl ring.

Hydration in fact involves formation of by-products, which can hardly be removed from the final product. Furthermore, the process by Kawai S. et al. requires the subsequent purification of the ketone of formula (B) by silica gel chromatography. This technique is unsuited to the production of large amounts of product, thereby making the whole process inapplicable on an industrial scale. The problem of by-products formation was substantially solved by EP 1260505 in which such hydration is carried out by means of a platinum, palladium or ruthenium catalyst, optionally in the presence of ligands. These catalysts are, however, very expensive, and significantly affect the final costs.

In view of this problem, EP 1616861 provides a process for hydrating the alkyne bond by use of a less expensive catalyst based on mercury (II) oxide in a $C_1$-$C_4$ alkanol. According to this process, the formation of difficult to remove by-products is further reduced thereby obtaining the corresponding keto compound in high yields.

The amount of mercuric oxide used in the process, that is already ⅒ of that one used by Kawai S. et al., typically ranges from 2 to 4 molar % referred to the substrate. The use of a mercury catalyst, however, is a problem, as it involves formation of wastes with such a mercury content that their disposal is troublesome; this increases costs and has a remarkable impact on the economy of the whole process.

There is therefore the need for an alternative process for the preparation of fexofenadine, which allows carrying out the hydration of the alkyne to the corresponding keto compound in the pure form, by using lower amounts of mercury while providing high yields.

SUMMARY OF THE INVENTION

It has now been found that the hydration reaction of the alkyne of formula (II), as herein defined, to obtain the corresponding derivative of formula (I), as herein defined, can be carried out in the presence of tetrahydrofuran by using a solution of a mercury (II) compound in $H_2SO_4$ approximately containing 1 molar % or less of the catalyst. Surprisingly, the yields obtained are still very high, and the mercury content in wastes is remarkably reduced as well. This makes the novel process of the invention very advantageous on an industrial scale.

BRIEF DESCRIPTION OF THE FIGURE

The FIGURE illustrates XRPD of 4-{[4-(4-hydroxydiphenylmethyl)-1-piperidinyl]-1-oxobutyl}-α,α-dimethylbenzeneacetic acid; (I).

DETAILED DISCLOSURE OF THE INVENTION

Object of the invention is a process for the preparation of a compound of formula (I)

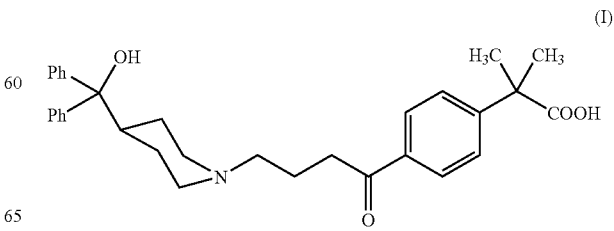

comprising the reaction of a compound of formula (II)

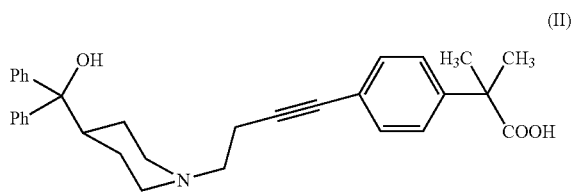

wherein Ph is a phenyl ring, with a sulfuric acid aqueous solution in the presence of a mercury (II) compound, in tetrahydrofuran.

A mercury (II) compound is typically a mercury (II) compound soluble in sulfuric acid, for example mercury (II) oxide.

The alkyne of formula (II) is reacted as a solution in tetrahydrofuran at a concentration from about 10 to about 40%, preferably approximately from 20 to 30% w/w.

The sulfuric acid aqueous solution is typically a solution having a concentration ranging from about 20 to about 50%, preferably from about 30 to about 40% w/w.

The reaction can be carried out by contacting the tetrahydrofuran solution of the alkyne of formula (II) with the sulfuric acid aqueous solution containing the mercury (II) compound, for example HgO.

The molar amount of sulfuric acid to the alkyne of formula (II) approximately ranges from 1 to 2; preferably from about 1.5 to about 1.8.

The molar amount of mercury (II) compound, for example HgO, to the alkyne of formula (II) approximately ranges from 0.6% to 1.6%; preferably around 1%, more preferably from about 0.8% to about 1.3%.

The reaction can be carried out at a temperature approximately ranging from 20° C. to the reflux temperature of the reaction mixture, preferably at about 60-66° C.

After completion of the reaction, the reaction mixture is alkalinized with a basic agent in aqueous solution, for example sodium hydroxide, the resulting salt of the keto of formula (I) is then transformed into the corresponding free acid by treatment with a mineral acid, e.g. hydrochloric, sulfuric or phosphoric acid, or an organic acid, e.g. acetic, methanesulfonic or oxalic acid. If desired, crystallization can be promoted by seeding with the previously obtained pure keto compound (I).

The resulting keto of formula (I): 4-{[4-(4-hydroxydiphenylmethyl)-1-piperidinyl]-1-oxobutyl}-α,α-dimethylbenzeneacetic acid, has a crystalline structure having an XRPD wherein the most intense diffraction peaks fall at 5.7; 8.8; 10.3; 11.5; 16.1; 17.3; 18.1; 19.4; 20.0; 22.8±0.20 in 2θ. The ketone of formula (I) in the crystalline form is a novel compound and is an object of the invention.

As it can be appreciated from the experimental example, according to
the process of invention less than half the amount of mercury (II) compound, for example HgO, is needed to provide a product having substantially the same purity characteristics while carrying out the process under operative conditions similar to those reported in EP 1616861; therefore the risk of mercury exposure for operators and the environmental impact are drastically reduced.

The keto compound of formula (I) can subsequently be reduced to obtain fexofenadine, of formula (III),

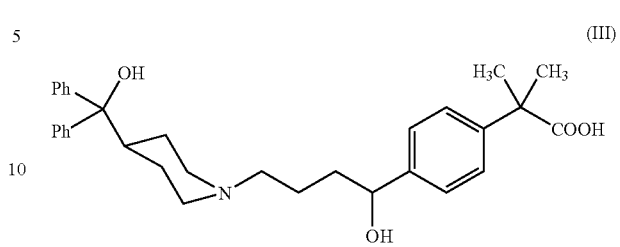

by known procedures, for example by a process comprising the reduction with a reducing agent, e.g. sodium borohydride, potassium borohydride, sodium cyanoborohydride or tetramethylammonium borohydride, in a suitable alkanol, e.g. methanol, ethanol, isopropanol, n-butanol or mixtures thereof with water, at a temperature approximately ranging from 0° C. to the reflux temperature of the reaction mixture. If desired, fexofenadine can then be converted to a salt thereof, for example the hydrochloride, according to known methods.

Therefore, the present invention also relates to a process for the preparation of fexofenadine, or a salt thereof, further comprising the reduction of a resulting keto compound of formula (I),

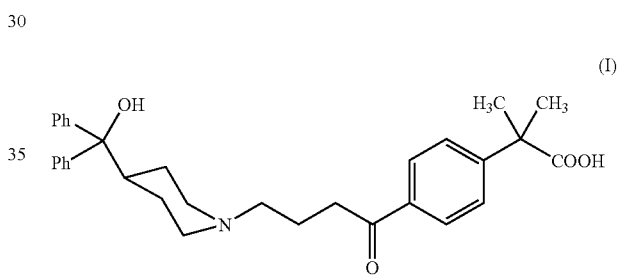

to obtain fexofenadine and, if desired, its conversion to a salt thereof. A fexofenadine salt is for example a pharmaceutically acceptable salt thereof, particularly the hydrochloride.

The following Example illustrates the invention.

EXAMPLE

Synthesis of 4-{[4-(4-hydroxydiphenylmethyl)-1-piperidinyl]-1-oxobutyl}-α,α-dimethylbenzeneacetic acid; (I)

A 3 L four-necked flask, equipped with stirrer, thermometer, cooler and kept under nitrogen, is loaded with 62.5 g of 4-{[4-(4-hydroxydiphenylmethyl)-1-piperidinyl]-1-butynyl}-α,α-dimethylbenzeneacetic acid and 250 g of tetrahydrofuran. A solution of 21.1 g of 96% w/w sulfuric acid in 40 g of water is prepared in a 100 ml round bottom flask, and added under stirring with 0.31 g of mercury oxide. The suspension of 4-{[4-(4-hydroxydiphenylmethyl)-1-piperidinyl]-1-butynyl}-α,αdimethylbenzeneacetic acid in tetrahydrofuran is added with the mercury sulfate aqueous solution prepared above. The resulting solution is heated to about 62-66° C. under stirring, keeping this temperature until completion of the reaction. (The yield, measured by titration in solution, is now higher than 90%). A solution of sodium hydroxide flakes (26.2 g) in 78.8 ml of water is prepared and added with the reaction mixture, at a temperature of 50° C. Then the resulting mixture is diluted with 62 g of tetrahydrofuran and 74.5 g of water, heated to the reflux temperature, and 9 g of glacial acetic acid are dropped therein. After adding about 30% of the acid, crystallization is promoted by seeding with the previously obtained pure keto compound (I), and the acid addition is completed. After that, the mixture is refluxed for about 15-20 minutes then cooled to about 15-30° C. in about 2 hours. The mixture is left at this temperature for about one hour and the solid is filtered and washed with tetrahydrofuran (2×100 ml). The resulting 4-{[4-(4-hydroxydiphenylmethyl)-1-piperidinyl]-1-oxobutyl}-α,α-dimethylbenzeneacetic acid has a crystalline structure having an XRPD wherein the most intense diffraction peaks fall at 5.7; 8.8; 10.3; 11.5; 16.1; 17.3; 18.1; 19.4; 20.0; 22.8±0.2° in 2θ. The solid is further purified from the inorganic salts by redissolution in 320 ml of methanol containing 4.9 g of sodium hydroxide flakes and reprecipitation with 7.7 g of acetic acid at 60-65° C. After cooling, the product is filtered, washed with water and methanol and dried. 51 g of product (I) in the above crystalline form are obtained; (purity above 99.5%; yield: 82%).

XRPD of 4-{[4-(4-hydroxydiphenylmethyl)-1-piperidinyl]-1-oxobutyl}-α,α-dimethylbenzeneacetic acid; (I).

As shown in the FIGURE, the novel form according to the invention was characterized with the usual XRPD technique (X-ray powder diffraction). X-ray diffraction spectrum (XRPD) was recorded with an automatic diffractometer for powders and liquids (Ital-Structures), under the following operative conditions: CuKα radiation (λ=1.5418 Å), scanning with angular step of 0.04° for 3 sec.

The XRPD (X-ray powder diffraction) diffractogram of the compound of formula (I) is reported in the FIGURE, wherein the most intense diffraction peaks fall at 5.7; 8.8; 10.3; 11.5; 16.1; 17.3; 18.1; 19.4; 20.0; 22.8±0.220 in 2θ.

The invention claimed is:
1. A process for the preparation of fexofenadine, the process comprising the steps of
(a) the reaction of a compound of formula (II)

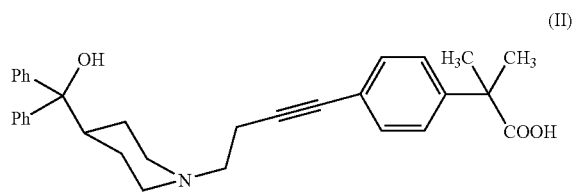

(II)

with an aqueous sulfuric acid solution in the presence of a mercury (II) compound, in tetrahydrofuran, to obtain a compound of formula (I)

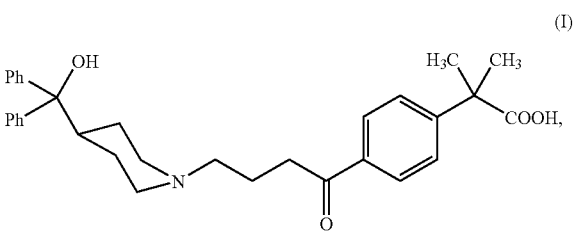

(I)

wherein the molar amount of mercury (II) compound to compound of formula (II) approximately ranges from 0.6% to 1.6%; and
(b) the reduction of a keto compound of formula (I) to obtain fexofenadine.
2. 4-{[4-(4-Hydroxydiphenylmethyl)-1-piperidinyl]-1-oxobutyl}-α,α-dimethylbenzeneacetic acid, in the crystalline form having an XRPD substantially as reported in FIG. 1, wherein the most intense diffraction peaks fall at 5.7; 8.8; 10.3; 11.5; 16.1; 17.3; 18.1; 19.4; 20.0; 22.8±0.2° in 2θ.
3. The process according to claim 1, further comprising the step of converting fexofenadine to a salt thereof.
4. The process according to claim 1, wherein the molar amount of mercury (II) compound to compound of formula (II) approximately ranges from 0.8% to 1.3%.

* * * * *